(12) United States Patent
Müller et al.

(10) Patent No.: US 9,398,975 B2
(45) Date of Patent: Jul. 26, 2016

(54) HAND-OPERATED COOLING DEVICE FOR CRYOTHERAPY

(75) Inventors: Stefan Müller, Spaichingen (DE); Steffen Ortlib, Spaichingen (DE); Ingo Dreher, Balgheim (DE)

(73) Assignees: Stefan Müller, Spaichingen (DE); Ingo Dreher, Balgheim (DE)

(*) Notice: Subject to any disclaimer, the term of this patent is extended or adjusted under 35 U.S.C. 154(b) by 955 days.

(21) Appl. No.: 13/640,777

(22) PCT Filed: Apr. 8, 2011

(86) PCT No.: PCT/EP2011/055486
§ 371 (c)(1),
(2), (4) Date: Dec. 29, 2012

(87) PCT Pub. No.: WO2011/141243
PCT Pub. Date: Nov. 17, 2011

(65) Prior Publication Data
US 2013/0103127 A1 Apr. 25, 2013

(30) Foreign Application Priority Data
Apr. 15, 2010 (DE) .......... 10 2010 016 458

(51) Int. Cl.
*A61F 7/00* (2006.01)
*A61M 19/00* (2006.01)
(Continued)

(52) U.S. Cl.
CPC .............. *A61F 7/0085* (2013.01); *A61M 19/00* (2013.01); *A61M 35/003* (2013.01); *F25D 9/00* (2013.01);
(Continued)

(58) Field of Classification Search
CPC .................. A61F 2007/0059; A61F 2007/006; A61F 2007/0063; A61F 2007/0064; A61F 2007/0087
See application file for complete search history.

(56) References Cited

U.S. PATENT DOCUMENTS 2,536,001 A 12/1950 Chase
2,709,431 A 5/1955 Claud
(Continued)

FOREIGN PATENT DOCUMENTS

DE 19548652 C2 12/1999
DE 20305694 U1 8/2004

OTHER PUBLICATIONS

International Search Report (Aug. 11, 2011) for corresponding International application No. PCT/EP2011/055486.
(Continued)

*Primary Examiner* — Joseph Stoklosa
*Assistant Examiner* — Nicole L Pobre
(74) *Attorney, Agent, or Firm* — WRB-IP LLP (57) ABSTRACT

A hand-operated cooling device for cryotherapy for treating pain, includes a main body and a receptacle, which can be inserted at least partially into the main body, for the exchangeable accommodation and insertion of a gas pressure vessel. The main body includes a manual gas outlet actuation arrangement, which can effects the outflow of a gas from the gas pressure vessel when the receptacle is inserted. The receptacle includes a cooling surface, which can be cooled by the outflowing gas and by the gas pressure vessel jacket, wherein the gas can be conducted inside the main body and inside the receptacle by a gas conducting arrangement and can exit at the receptacle adjacent to the cooling surface. Commercially available gas pressure vessels, can be inserted into the cooling device, so that a simple and cost-effective use of therapeutic OT medical cryotherapy having a pleasant cooling effect is made possible.

12 Claims, 9 Drawing Sheets

(51) Int. Cl.
*A61M 35/00* (2006.01)
*F25D 9/00* (2006.01)
*A61M 5/44* (2006.01)

(52) U.S. Cl.
CPC . *A61F 2007/0064* (2013.01); *A61F 2007/0087* (2013.01); *A61M 5/44* (2013.01); *A61M 2202/0225* (2013.01); *A61M 2202/0283* (2013.01); *A61M 2202/03* (2013.01); *A61M 2205/3606* (2013.01); *A61M 2205/8225* (2013.01)

(56) References Cited

U.S. PATENT DOCUMENTS

| 2,746,264 | A | 5/1956 | Keyes |
| 2006/0178716 | A1 | 8/2006 | Leason et al. |
| 2008/0142036 | A1 | 6/2008 | Sanchez |
| 2009/0248001 | A1 | 10/2009 | Burger et al. |

OTHER PUBLICATIONS

DE69918810 (Aug. 11, 2005) Cryo Medical, abstract plus document.
DE60109801 (Feb. 16, 2006) Cryonic Medical, abstract plus document.

HAND-OPERATED COOLING DEVICE FOR CRYOTHERAPY

BACKGROUND AND SUMMARY

The present invention is based on a hand-operated cooling device for cryotherapy for the treatment of pain, inflammation, muscle tension or the like, comprising a main body and a receptacle that can be at least partially inserted in the main body for the exchangeable receiving and retaining of a gas pressure vessel.

Cryotherapy is the targeted use of cold energy to bring about a therapeutic effect. In particular with injuries to internal muscles, fibres or tendons, as can occur in sport for example, cooling of the affected area from the outside by means of a cooling device can bring rapid relief as well as speed up a healing process. It is important to cool the affected area externally as soon as possible after the occurrence of the injury. It is particularly advantageous here to cool the epidermis, i.e., the outer skin layer, of the area to be treated to a temperature of approximately 2 to 5° C., at which the cold has a maximum effect on the skin receptors and thereby acts to reduce pain and inhibit blood flow in order to bring about a rapid healing of the internally damaged area.

Most cryotherapy devices use as the cold source either cooled air or liquid nitrogen, which is sprayed directly onto the affected area and has a very unpleasant effect, since a sudden cold effect is generated over a large area, is difficult to meter and can generate wet areas on the skin due to condensation. It is also known how to use gas cartridges under low pressure which achieve pressure relief in the immediate vicinity of a local trauma at a temperature of down to −25° C., with a temperature difference of this type possibly causing local cold burns.

A hand-operated cryotherapy spray device is known from DE 601 09 801 T2 in which gas, for example $CO_2$, is sprayed from a gas pressure vessel directly onto the area of the epidermis to be cooled. A cold spray device of this type has the advantage that an instant cooling effect can occur, because the expanding gas flows directly to the area to be cooled. However, upon conclusion of spraying from the gas pressure vessel, the cooling effect ceases immediately. The condensation effect of the gas results in very substantial wetting of the area to be cooled, since the expanding gas is converted into a liquid aggregate state. If too much gas exits the device, then there is the risk of cold burns. To ensure a prolonged cooling effect, it is necessary to carry a very large gas pressure vessel, which increases the dimensions of the cooling device and thus disadvantageously prevents it from being used flexibly and carried easily.

US 2009 02 480 01 A1 discloses a hand-operated cooling device, wherein a probe needle is pushed through the surface of a skin. A cooling fluid is passed through the probe needle by means of an electrical control system for cooling purposes. The cooling fluid can be provided by an $N_2O$ cartridge.

DE 699 18 810 T2 describes a cooling device which contains a $CO_2$ cartridge, where the $CO_2$ gas can exit through an opening of the cooling surface. The cooling device is actuated by an electric valve and the cartridge projects out of the device.

A cooling device with a $CO_2$ capsule is known from DE 195 48 652 A1, through which cold can be applied by outflowing gas by means of a heat exchanger. The device comprises electronic components such as digital thermometers. The capsule is not accommodated inside the housing of the device.

Lastly, a cooling device is disclosed in DE 203 05 694 U1 with an insertable gas cartridge from which a cooling gas can be released by mechanical actuation of a valve. The released cooling gas can be directed towards a skin region to be cooled.

U.S. Pat. No. 2,536,001 A describes a cooling device with a cartridge containing a cooling means and comprising a receptacle and a main body with cooling agent outlet actuating means. The cooling agent expands inside the cooling agent device and cools a cooling surface that is arranged on an axial end of the main body. The cooling gas is released at a release surface of the receptacle that is arranged axially opposed to the cooling surface of the main body.

The cooling device is consequently relatively large since the cooling gas expands internally in order to cool the cooling surface which lies at a distance from the gas release point.

DE 195 48 652 C discloses a cooling device for cryotherapy in which the gas for cooling can be applied to the skin, where the gas release time and the distance of the gas outlet nozzle from the skin is electronically adjustable.

DE 203 05 694 U discloses a further generic cryotherapy device that has a gas outlet actuating means for the direct effect of cooling agent on the skin, where a securing mechanism has to be disengaged for actuation of the gas release actuation means.

US 2008 142036 A discloses a cooling device in which a cooling surface of a main body is of metal and a receptacle consists of or comprises thermally insulated material such as plastic with a thermal conductivity below 1 $Wm^{-1}K^{-1}$.

It is desirable to propose a portable hand-operated cooling device which does not supply gas directly to an area to be cooled while preventing incorrect handling or the danger of frostbite, which provides a constant, prolonged cooling effect yet has only small dimensions and is portable. It is also desirable to achieve a cooling effect by means of gas pressure vessels which are available in high quantities and at low cost in order to keep the service life and the operating costs low.

The present invention is based on a hand-operated cooling device for cryotherapy for the treatment of pain, inflammation, muscle tension or the like, comprising a main body and a receptacle that can be at least partially inserted in the main body for the exchangeable receiving and insertion of a gas pressure vessel. The present invention proposes that the main body has a gas outlet actuating means which can be actuated manually, which can bring about outflow of a gas from the gas pressure vessel when the receptacle is in place, and that the receptacle has a cooling surface which can be cooled by the outflowing gas and by the gas pressure vessel jacket, with the gas being conducted inside the main body and inside the receptacle by gas conducting means and can exit at the receptacle adjacent to the cooling surface. In other words, the present invention proposes that a cooling device having at least two parts consists of or comprises a main body comprising a gas outlet actuating means by which it gas can be released from a gas pressure vessel. The gas pressure vessel is accommodated in a receptacle which is then inserted into the main body such that upon actuation of the gas outlet actuating means the gas flows out of the gas pressure vessel and is conducted inside the main body and the receptacle by gas conducting means in such a way that it can flow out next to a cooling surface on the receptacle, in particular the bottom surface of the receptacle, to cool the cooling surface. It is essential here that the outflowing gas is not released in the direction of the cooling surface, but to the side or upwards away from the cooling surface, so that the surface to be cooled is not directly aerated or sprayed with the gas. The expansion effect of the gas from the gas pressure vessel on the one hand results in cooling due to the expansion effect along the gas conducting means, and on the other the gas pressure vessel is substantially cooled by the expansion, with the gas pressure vessel is in most cases being made of metal, in particular aluminium or a similar material. If gas flows out of the gas pressure vessel, the pressure P inside the gas pressure vessel is considerably reduced at constant volume V according to the formula $$\frac{P \cdot V}{T}$$

Since the volume remains constant, the temperature T must accordingly also be reduced, which greatly cools the gas pressure vessel. The cooling of the gas pressure vessel and expansion of gas inside the cooling device generates cold which is absorbed by the receptacle, which for this purpose preferably consists of or comprises a material that is a good conductor of heat, for example a metal, and hence cools the cooling surface arranged on the outer surface. Any quantity of cold can be stored, depending on the heat storage capacity of the receptacle and the gas pressure vessel, and passed to the cooling surface. Depending on the control of the outflow rate of the gas, the temperature change and hence the temperature occurring at the cooling surface can be pre-determined such that in particular an advantageous cooling temperature of 2-5° C. can be attained at the cooling surface. If the entire assembly has a high thermal capacity, then this cooling effect can be maintained over a long period of time, for example from 3 to 10 minutes. The expanding gas does not flow directly to the area to be cooled, but instead flows indirectly and serves only to relieve the pressure in the gas pressure vessel and to cool the entire cooling device/the cooling surface of the receptacle. If the gas outlet actuating means on the main body is actuated, then gas can flow out over a period of 2 to 30 seconds and is released indirectly in the vicinity of the cooling surface, and the cooling surface/entire receptacle can be cooled to a temperature of approx. 2 to 10° C., where this temperature can be maintained for a period of 3 to 5 minutes. The device can be operated very easily by a layperson because the cooling device is in just two parts and the gas pressure vessel can be readily inserted into the receptacle that can be inserted or screwed into the main body. The dimensions of the cooling device can differ to only a minor degree from those of the gas pressure vessel used, so that when a small gas pressure vessel is used, for example a 8 g, cream capsule, a very small "cooling stick" will result which can be carried everywhere and can be used flexibly. The proposed cooling device is therefore very small and is simple to use, with no danger of cold burns. The device is thus very mobile, can be used in a space-saving manner and can be refilled, and generates a constant cold effect over a long period of time. The cooling device is designed for a large number of therapy applications and has a long service life.

In accordance with an advantageous embodiment, the receptacle is designed substantially cup-shaped and complementary in shape to the bottom region of the gas pressure vessel and is made from a material that has a high thermal conductivity, preferably metal, with the bottom outer surface of the receptacle forming the cooling surface. Furthermore, the receptacle can have at least one and in particular a plurality of gas outlet ducts along a jacket circumferential region at the bottom end, and the receptacle can accommodate the gas pressure vessel at least in the bottom region substantially with positive fit to attain good heat coupling, where between the inner wall of the receptacle and the outer gas pressure vessel outflowing gas can flow from the open end of the receptacle inserted into the main body to the gas outlet duct or ducts preferably along one or more gas conducting means, in particular gas guiding ducts. This further development thus represents an advantageous embodiment of the receptacle, which is made from a material of high thermal conductivity, preferably metal. The receptacle can advantageously be designed cup-shaped and complementary in shape to the underside (bottom region) of a gas pressure vessel, in particular a cream capsule that is commercially available or a cartridge for a $CO_2$ water dispenser, with the bottom outer surface of the receptacle at the same time forming the cooling surface. With the receptacle inserted into the main body, this bottom surface that forms an axial end of the cooling device that substantially cylindrical in shape can be placed on an area to be treated. The bottom surface can be flat, pointed or rounded to provide cooling effects over large areas or point areas. A rounded cooling surface in particular can be used for both punctiform and large-area cooling of soft tissue, depending on the pressure exerted. The gas conducting means can be, for example, gas guiding, ducts that extend inside the outer wall of the receptacle, however the gas conducting means can also be a gap between the gas pressure vessel jacket and the inner surface of the receptacle, where the gas can flow along the jacket surface of the gas pressure vessel and exit in the vicinity of the cooling surface at the bottom end of the receptacle through gas outlet ducts. It should be noted here that the gas outlet ducts guide the gas out of the cooling device in such a way that there is no direct spray effect on the epidermis to be cooled and to which the cooling stick is applied. The gas exits inside the main body, which has a gas outlet actuating means, for example a penetrating pin, which pierces a sealing cap of the gas pressure vessel, with the gas inside the main body being conducted into the upwardly-open end of the receptacle and then further conducted inside the receptacle to the bottom end of the receptacle where it can exit. The cup-shaped arrangement of the receptacle enables a very simple use or change of gas pressure vessels for the cooling device without special instruction.

In accordance with a further advantageous embodiment, the receptacle with gas pressure vessel in place can be introduced into the main body by means of screws, by a snap fit or by a bayonet fitting. Following accommodation of a gas pressure vessel in the preferably cup-shaped receptacle, the latter must be inserted in the main body for activating the cooling effect, where the main body with gas outlet actuating means brings about outflow of the gas and cooling of the jacket of the gas pressure vessel, and this cooling effect can be exerted via the outer jacket of the receptacle, in particular the cooling surface, onto an area to be treated. The receptacle and main body can be connected by a screw connection or a snap-in connection, where for example a re-openable snap-in connection between the receptacle and the main body can be achieved. Finally, a bayonet connection is also conceivable in which guide lugs of the counter-piece are introduced into an obliquely-extending groove of the main body or receptacle, then turned and brought into a fixing position. It is essential that the connection mechanism between the receptacle and the main body is designed to absorb high forces, since high pressure escape forces occur during gas expansion and upon throttling of the gas outlet these forces have to be withstood by a non-positive connection between the receptacle and the main body. An unsecured connection between the receptacle and the main body can lead to an explosive expulsion of both parts of the cooling device, which must be avoided at all costs.

In accordance with a further advantageous embodiment, the gas outlet actuating means can comprise a rotating, rocker, press or pull outlet mechanism to bring about an outflow of gas from the gas pressure vessel, where after insertion of the gas pressure vessel the outlet mechanism can actuate shut-off valve of the as pressure vessel by a rotating, rocker, press or pull movement of an actuating element. Hence with both these alternative embodiments of the gas outlet actuating means, insertion of the receptacle in the main body already results in an opening of the gas pressure vessel, as a result of which gas flows into the cooling device. A shut-off valve can be arranged for a gas-tight design of the gas conducting means, where for example the gas can be conducted through gas conducting means along the gas pressure vessel by actuation oldie shut-off valve and be emitted by gas guiding ducts to achieve a cooling effect. Alternatively to this, a previously closed membrane or a valve arranged on the gas pressure vessel can be actuated by actuation of the gas outlet actuating means in order to bring about the outflow of gas. The gas outlet actuating means can thus comprise either a shut-off valve to regulate the volume of outflowing gas and/or an opening means to open a sealing membrane of the gas pressure vessel. Furthermore, the gas outlet actuating means can comprise an outflow mechanism which for example is in the form of a rotating, rocker, press or pull mechanism for actuating the corresponding shut-off valve or the corresponding opening element to pierce the sealing membrane. The gas outlet actuating means can comprise, for example, a screw connection, in which by turning an opening pin element pierces a sealing membrane of the gas pressure vessel or actuates a gas outlet valve. Instead of a rotating effect, a pressure effect on a pressure cap can enable opening of the gas outlet valve at the same time. Alternatively, a rocker mechanism or a pull mechanism can also enable piercing of the sealing membrane or an actuation of a shut-off valve or both.

According to a further advantageous development, the gas outlet actuating means can comprise an opening pin for penetrative piercing of the sealing membrane of the gas pressure vessel. This opening pin can be accommodated in particular in an opening pin element and achieve by said opening movement penetrative piercing of as sealing membrane of a gas pressure vessel, in particular a conventional cream capsule or air pressure cartridge.

In principle, outflow of gas can be instantaneous and unhindered after actuation of the gas outlet actuating means, so that a high cooling effect is achieved by means of a complete escape of the gas. In an advantageous development of the invention, the main body can preferably have at least one gas passage aperture designed to reduce the gas exit velocity, where the gas passage aperture preferably has an adjustable orifice diameter d, so that the gas exit velocity and hence the required cooling temperature is preferably in the range of 2 to 12° C., in particular from 5 to 7° C. A gas passage aperture of this type acts as a gas flow restrictor and restricts the speed at which the gas can flow out of the compressed gas cartridge. By specifically influencing the flow velocity, the duration up to the complete emptying of the gas pressure vessel can be adjusted, whereby the final temperature to be reached and the duration of the cooling process can be directly influenced. An aperture of this type may have a fixed diameter d, which can be designed for the above temperature ranges. However it is also conceivable for the aperture diameter d to be designed adjustable such that, depending on the application, a high (short) cooling effect or low (long-lasting) cooling effect can be achieved by adjusting the gas outflow volume. Furthermore, it is also conceivable when using a shut-off valve or an aperture functioning as a valve for not all of the gas to flow out, so that repeated use of the cooling effect can be achieved with a single gas pressure vessel in particular at low flow rates.

According to an advantageous development of the invention, the outlet mechanism of the gas outlet actuating means can comprise a securing element which can prevent an unintentional actuation of the actuating element. A securing element of this type prevents in particular during portable use, for example in an emergency bag or under difficult conditions, such as when used in sport, during travel, etc. inadvertent triggering of the gas outlet actuating means and hence unintentional use of the single-use cooling effect of the cooling device. These securing means can be, for example, a locking pin or a locking push button ensuring a locked position of the outlet mechanism so that it is not inadvertently activated without actuation of the safety button or pulling out the safety pin. A robust handling is thus enabled and prevents incorrect operation of the cooling device.

According to an advantageous development of the invention, the receptacle is suitable for accommodating a $N_2O$ (nitrous oxide) or $CO_2$ (carbon dioxide) gas pressure vessel with a fill weight of 2 to 350 g, preferably from 6 to 20 g, in particular 8 g, which may have a length dimension of 4 to 20 cm, in particular 6 to 7 cm and a diameter of 1 to 7 cm, in particular 1 to 2.5 cm. This further development thus proposes the use of a commercially available $N_2O$ or $CO_2$ gas pressure vessel, as for example in the use of water carbonators, for cream whisking, in gas pressure shooting sport of for the cooling of beverage machines, in receptacles that are universally usable and inexpensively available in large quantities, where the fill weight of the gas pressure vessel directly influences the cooling temperature and the cooling period that can be achieved. The larger the gas pressure vessel, the lower the temperature that can be attained and/or the longer the cooling effect. Small gas pressure vessels of 8 g in particular, which generally have a length of 5 to 7 cm and a diameter of 1 to 2 cm, are exceptionally well suited to use in hand-operated cooling devices since they permit small dimensions of the cooling device, so that it is transportable, for example in trouser pockets or in an emergency kit, can be carried compactly and can be used whilst travelling.

Particularly preferably, the gas pressure vessel can be a commercially available $CO_2$ 8 g cream dispensing cartridge, in particular an ISI cream cartridge available on the market in large quantities at favourable prices. A cream cartridge is readily available virtually everywhere in supermarkets and can be used economically in the cooling device and be carried around.

Regarding the material selected for the cooling device, the main body can be manufactured from any desired material, where in particular the cooling surface of the receptacle should be of a material with a high thermal conductivity. It is particularly preferred for the cooling surface of the receptacle to be of a material of high specific thermal conductivity, preferably metal, in particular an aluminium alloy such as AlMgSi and for the main body and remaining parts to be of a material of low specific thermal conductivity, i.e., with a high insulation effect, in particular heat-insulating plastic, preferably polyoxymethylene (POM), where a handling region of the main body is preferably additionally heat-insulating by an insulating layer. Hence the main body in particular can be fabricated from a heat-insulating material, in particular a favourable plastic, where the handling region is particularly insulated to protect the user against the cold effect when using the cooling device. The cold effect should be exclusively emitted an outward direction at the cooling surface of the receptacle, hence this cooling surface and the surrounding material have a high thermal conductivity, in particular a high electrical conductivity, and have a large thermal storage capacity so that the cooling temperature can be stored and discharged over a lengthy period. It is thus proposed with this embodiment that large areas of the cooling device are designed heat-insulating, so that the cold that can be generated is formed in particular in the gas pressure vessel jacket, and can be discharged only via the cooling surface to the outside, so that an efficient and lasting cooling effect can be achieved.

High gas flow rates and large gas pressure forces result upon outflow of the gas from the gas pressure vessel. To achieve a high durability of the cooling device, it is advantageous if the parts acting in the cooling stream of the gas outlet are designed to be particularly durable. Therefore it is proposed in an advantageous development that the opening pin, in particular an opening pin element, is of a durable material, especially steel, for example X20Cr13. By the design of the opening pin, which serves to pierce a sealing membrane of a gas pressure vessel or to open a valve integrated into the gas pressure vessel, an opening pin element is thus proposed which is suitable to pierce a thick sealing membrane or to actuate a stiff gas valve of a gas pressure vessel and which can absorb the high outflow forces and the attained cooling effect inside the cooling pin and which is of particularly robust design for a long service life and a high throughput volume.

According to a further advantageous embodiment, which is important in particular for the design of the cooling device and which is designed for a long service life, low production costs as well as good transportability and handling of the cooling device, the main body can be designed in several parts and in particular can comprise a cap, a handle, a receiving element, a sealing element, a bell element and an opening pin element, where at least the cap, the sealing element, the bell element and the opening pin element are positively connected to one another to form a gas outlet actuating means. Furthermore, a hand guide element can comprise at least one handle and a receiving element which are positively connected to each other, so that the hand guide element serves to receive the receptacle and to control the cooling device by a user. Thus it is proposed with this further development that the main body in principle is designed in two parts, where the one part is constructed as a gas outlet actuating means comprising a plurality of multi-part functionally interlocking and positively connected parts. Furthermore, the second part of the main body comprises the hand guide element, a receiving mechanism to receive the receptacle and to pass on the gas into the receptacle after exit in the gas outlet actuating means. It is particularly advantageous here when the gas outlet actuating means is mounted to be displaceable relative to the hand guide element, in particular rotatable for the purpose of performing an actuating movement for a penetrative piercing of a sealing membrane of an accommodated gas pressure vessel or to open a valve inside the gas pressure vessel. Thus in this further development it is proposed that the main body is substantially in two pans and comprises a gas outlet actuating means as an axial end piece and a hand guide element for hand control and receiving of the receptacle. These two parts in turn comprise a plurality of functionally and structurally interlocking individual components that can withstand a high gas pressure and are of heat-insulating design. The gas outlet actuating means is advantageously displaceable relative to the hand guide element to bring about gas release from the gas pressure vessel, in particular it can be rotated so that the opening pin element of the gas outlet actuating means pierces a gas pressure vessel accommodated in the hand guide element.

BRIEF DESCRIPTION OF THE DRAWINGS

Further advantages are derived from the description of the drawings. The drawings show embodiments of the invention. The drawings, the description and the claims contain numerous features in combination. A person skilled in the art will expediently also view the features individually and group them to form meaningful further combinations.

The drawing shows in.

DETAILED DESCRIPTION

Components which are the same or are of the same type in the FIGures are designated by the same reference numbers.

Figure 1:
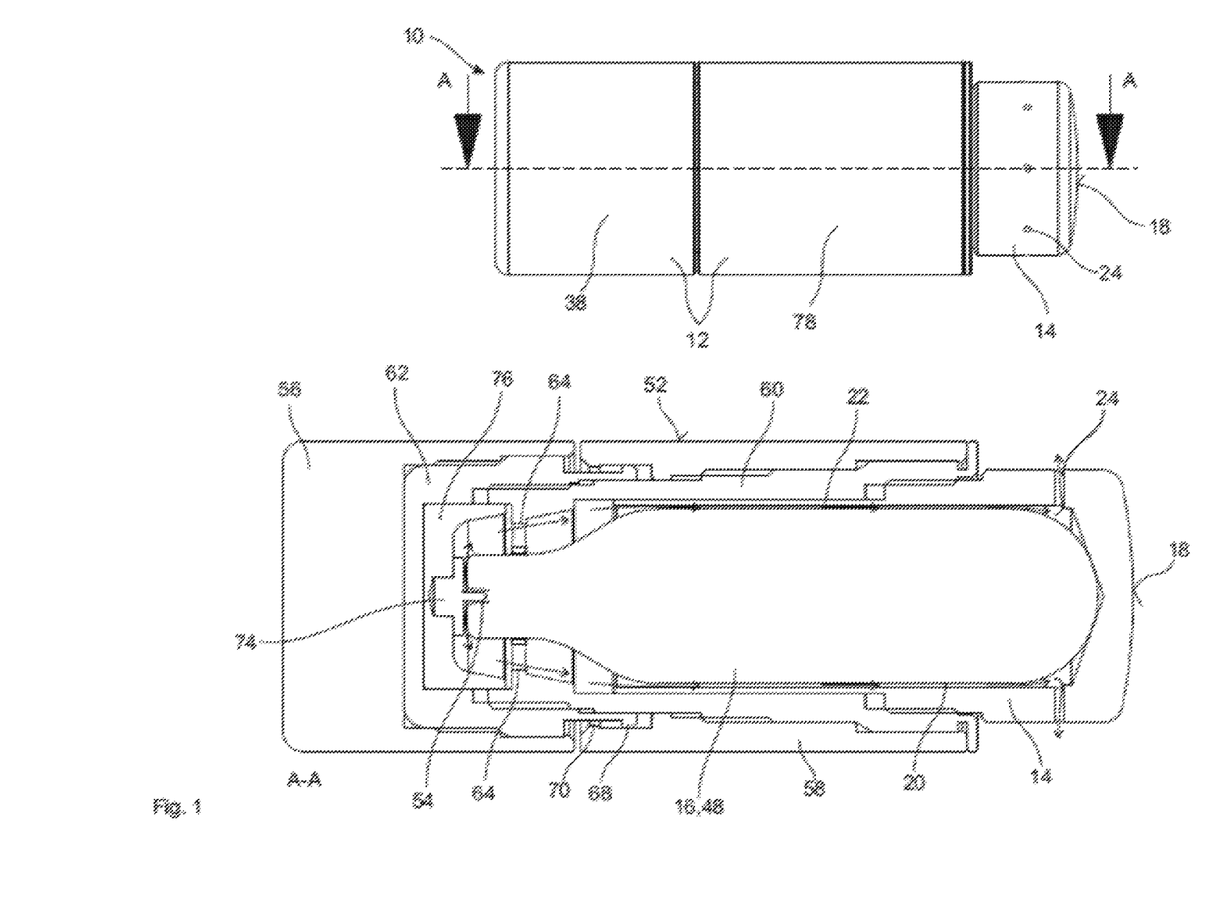
FIG. 1 a side view and a section through a first embodiment of a hand-operated cooling device.

FIG. 1 shows a side view, as well as a section A-A through a first embodiment 10 of a hand-operated cooling device for cryotherapy. The cooling device 10 essentially comprises a main body 12, which is made up of an actuating element 38 and a hand guide element 78, as well as a receptacle 14 serving to hold a gas pressure vessel 16, in this case a cream capsule 48, and which can be inserted, in particular screwed, into the main body 12. The actuating element 38 of the main body 12 comprises a cap 56, a sealing element 62 and a bell element 76, which comprises an opening pin element 74. The actuating element 38 is arranged rotatably mounted on the hand guide element 78 by means of a fine thread and locking elements 68, 70, in particular locking rings, so that it can be displaced longitudinally by a rotational movement axially back and forth, where the movement direction is limited by the locking elements 68, 70 in both directions. The hand guide element 78 comprises a handle 58 as well as a receiving element 60 screwed into the handle, which serves to hold the receptacle 14. The receptacle 14 accommodates on its bottom side a cream capsule 48 and is screwed by means of a fine thread into the receiving element 60 of the hand guide element 78. If the actuating element 38 is screwed in axially relative to the hand guide element 78 by means of a rotational movement such that it moves in the direction of the hand guide element 78, then an opening pin 54 of the opening pin element 74 pierces a sealing membrane 44 of the cream capsule 48/opens its head-side valve. Here, as indicated by arrows, gas exits the cream capsule 48 and flows around the inner region of the bell element 76, flows through the gas passage apertures 64 of the receiving element 60, and flows in the intermediate space between the inner surface of the receiving element 60 and the gas pressure vessel jacket 20 into the bottom region of the receptacle 14, where the gas can escape through gas conducting ducts 24 to the outside, without reaching the place to be cooled. On the bottom of the cup-shaped receptacle 14, a cooling surface 18 is arranged. The controlled release of the gas from the cream capsule 48 causes a relatively strong cooling of the gas pressure vessel jacket 20, with the flowing gas also generating a cold effect along the inner surface of the receptacle 14. Since the main body 12 is comprised of a thermally insulating plastic, this cold cannot reach the outside, particularly in the hand guide region 52, so that in particular the bottom side and hence the cooling surface 18 of the receptacle 14 of metal, especially aluminium, is cooled very substantially, since the cold can only escape here. The cooling surface 18 can be guided to a place to be treated and there the cold can be released, for example to painful muscles, tendons or ligaments. The gas is not released directly to the place to be treated, but laterally through a plurality of small gas outlet ducts, which are equally spaced on the jacket circumference on the bottom of the receptacle 14. By this it is avoided that the gas directly contacts the epidermis to be treated, so that there is no unpleasant cooling effect and cooling can be regulated selectively by hand guidance. If the opening pin 54 pierces the membrane of the cream capsule 48, then the gas is completely released from the gas pressure vessel 16, so that a single cooling effect can be achieved. After replacement of the gas pressure vessel by unscrewing the receptacle 14 from the main body 12, a further cream capsule can be received and the receptacle 14 placed in the main body 12, so that, by screwing the cap 56 in the direction of the hand guide element 78 a further cooling effect can be brought about. It is important here that prior to replacement of the gas pressure vessel 16 the actuating element 38 is unscrewed/reset relative to the hand guide element 78, so that there is no danger of immediate gas release when screwing the receptacle 14 into the main body 12.

Furthermore, it is conceivable that the actuating element 38 comprises a valve, where for example upon insertion of the receptacle 14 into the main body 12 the sealing membrane 44 of the gas pressure vessel 16 is immediately pierced and where said penetration region is gas-tight and only upon opening of the shut-off valve arranged in the actuating element can gas be released. Alternatively, the gas pressure vessel 16 can comprise a head-side valve, where suitable actuation means are arranged inside the actuating element 38 which can open the valve to bring about a gas release. The use of a shut-off valve has the advantage that in particular with a sufficiently large volume of gas of the gas pressure vessel 16 there is not a single release of gas, but instead a repeated metered cooling effect can be achieved with an adjustable cooling temperature. The shape, number and diameter of the gas passage apertures 64 of the receiving element 60 substantially determine the speed at which the gas can flow out and hence the cooling temperature to be reached. It is conceivable to make the diameter of the gas passage aperture 64 or the number of the open apertures 64 adjustable, for example by means of a knurled screw and a displaceable aperture masking element so that the gas release volume and flow rate and hence the cooling temperature to be reached can be adjusted externally. Gas-tight seals can be deployed between the various glands and connecting elements of individual parts of the cooling device, which can prevent an unwanted outflow of the gas at the connection/screw points.

Figure 2:
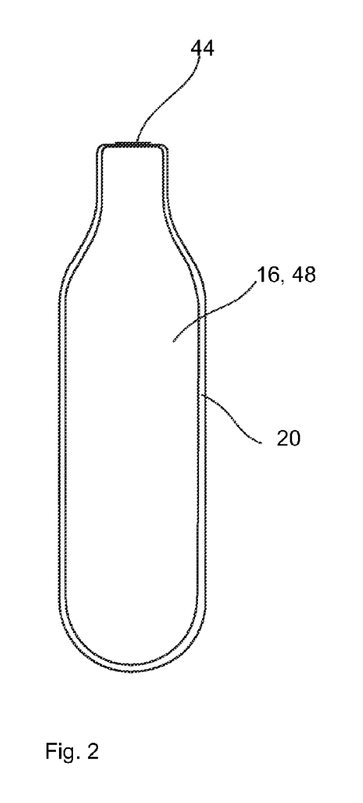
FIG. 2 a section through a gas pressure vessel that can be inserted into a cooling device in accordance with the invention.

FIG. 2 illustrates a section through a gas pressure vessel 16, in particular through a cream capsule 48, which is suitable for insertion into a hand-operated cooling device 10 of the invention. The gas pressure vessel 16 comprises a gas pressure vessel jacket 20, which is usually made of metal, in particular aluminium, and which has a high thermal capacity. At the top end of the gas pressure vessel 16, a sealing membrane 44 of thin vessel jacket material is arranged which can be easily pierced by an opening pin 54. When gas is released under pressure from the gas pressure vessel, in particular $CO_2$ or $N_2O$, the gas expands, while the temperature falls. The outflowing gas hence produces a cooling effect, with the gas pressure vessel jacket cooling considerably. If the gas pressure vessel 16 is enclosed by insulating material and is surrounded only at its bottom end with inserted receptacle by the receptacle material, which has a good thermal conductivity, then virtually all of the cold generated on the cooling surface 18 of the bottom side of the receptacle 14 is dissipated. A high codling effect and, depending on the release velocity and volume of the gas, a pleasant 2 to 5° C. results for the treatment of painful parts of the body.

Figure 3:
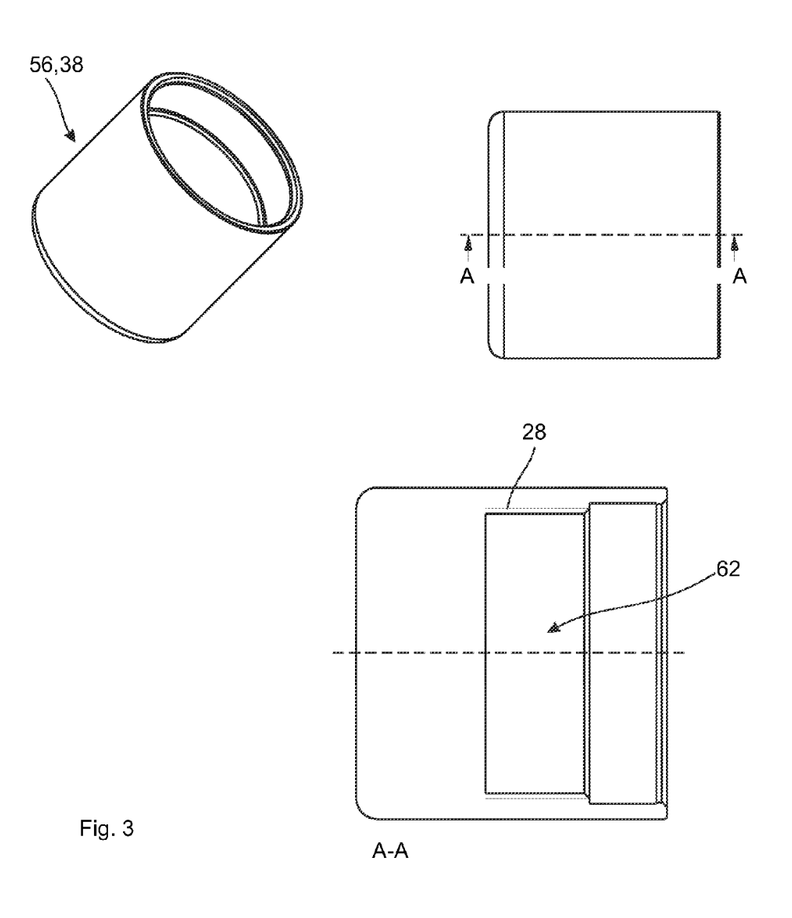
FIG. 3 different representations of a cap of the first embodiment.

FIG. 3 shows, in a perspective three-dimensional representation, as well as a side and sectional view A-A, the structure of the cap 56 forming the outer region of the actuating element 38. The cap 56 has an axial end opened on one side in which a thread 28 is attached to the inner jacket surface and which is shaped such that a sealing element 62 can be screwed into it.

Figure 4:
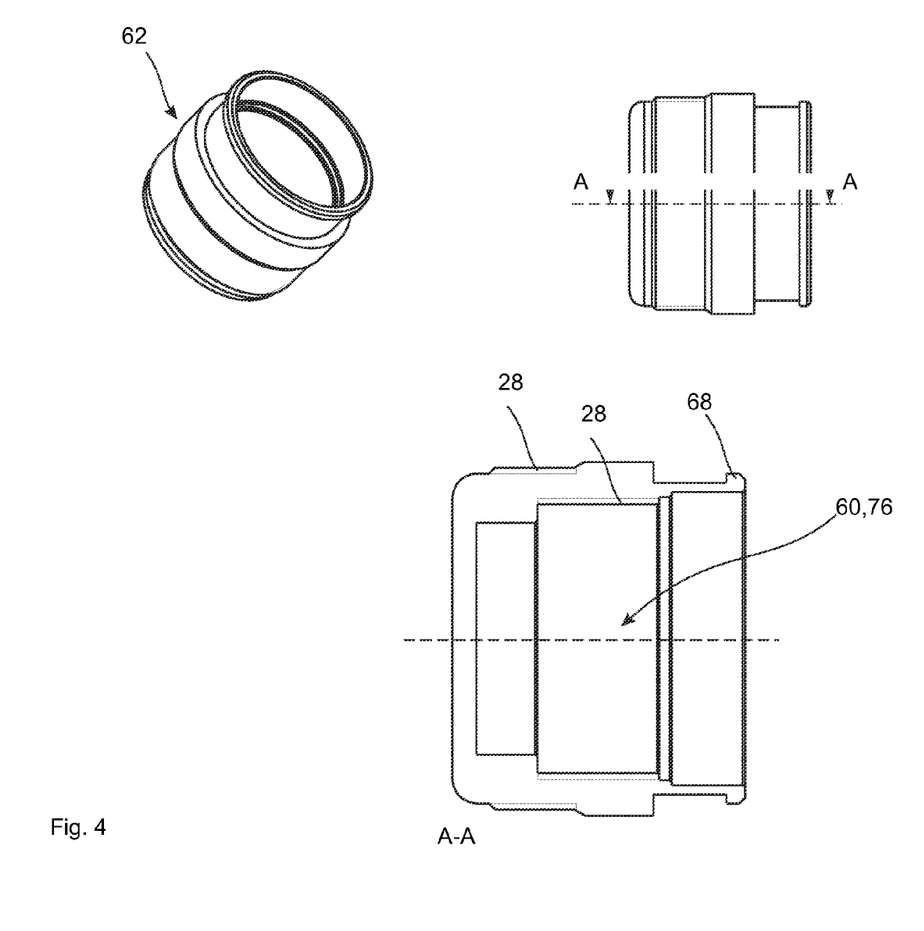
FIG. 4 different representations of a sealing element of the first embodiment.

FIG. 4 shows, in a further multi-perspective view, the arrangement of a sealing element 62 of the first embodiment of FIG. 1. The sealing element 62 has on its outer jacket surface a fine thread 28 so that it can be screwed complementary in shape into the cap 56. Internally, the sealing element 62 has a further line thread 28, where a bell element 76 with inserted opening pin element 74 can be inserted, pressed into or bonded to a recess in a shape-complementary manner, as well as a receiving element 60. Furthermore, it has at its axially open end on the outer surface a locking ring 68 which causes a locking action and hence defines a limited travel distance with respect to the hand guide element 78.

Figure 5:
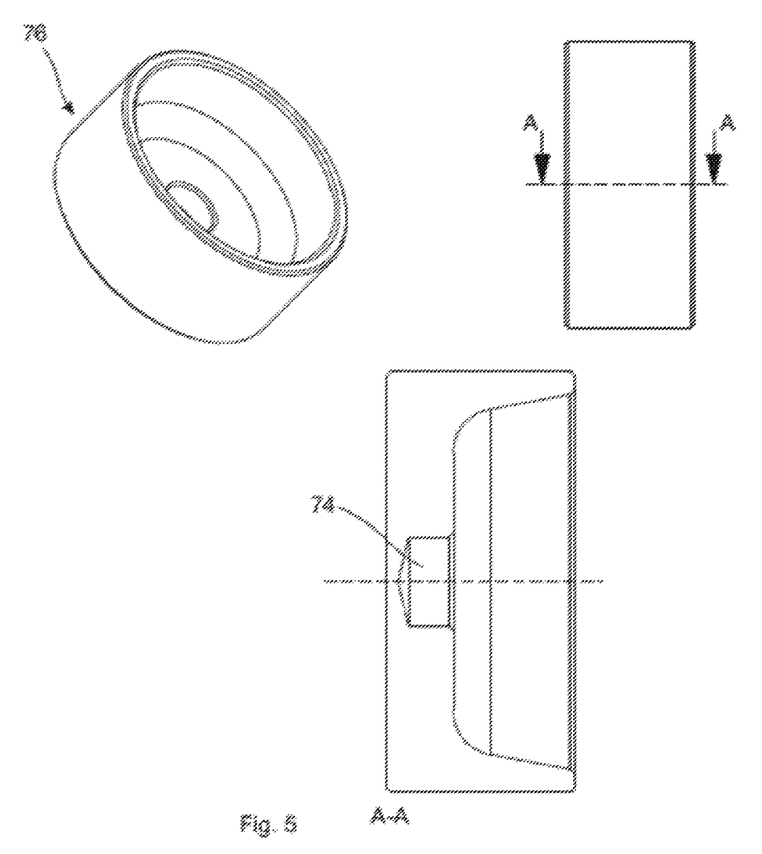
FIG. 5 different representations of a bell element of the first embodiment.

FIG. 5 shows both a perspective view and a lateral and sectional view A-A of an embodiment of a bell element 76. The bell element 76 is in turn axially half-side open, and comprises a receiving area into which an opening pin element 74 can be inserted, and furthermore a bell region which serves to guide the released gas along the space between the gas pressure vessel jacket 20 and the inner surface of the main body 12 and receptacle 14. The bell element 76 can be inserted, for example positively by means of press fit, into the sealing element 62, or glued.

Figure 6:
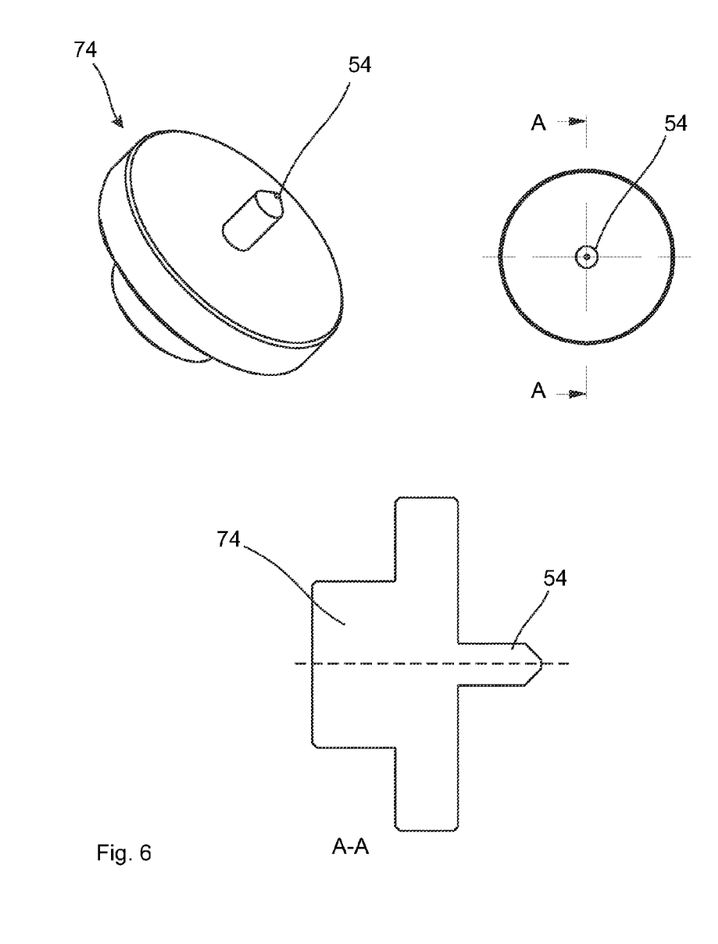
FIG. 6 different representations of an opening pin element of the first embodiment.

Finally, FIG. 6 shows in a perspective view and in a plan view and side view an opening pin element 74 of the first embodiment 10. The opening pin element 74 has on its side facing in the direction of the receptacle 14 an opening pin 54 which is adapted for penetrative piercing of a sealing membrane 44 or for actuating a shut-off valve of a gas pressure vessel 16, Accordingly, the opening pin element 74 is of a robust material, such as steel, to withstand the high released gas pressure forces and the high opening forces, and to prevent blunting of the opening pin 54. The opening pin element 74, bell element 76, sealing element 72 and cap 56 form in their assembled form the actuating element 38 of the main body 12 of the first embodiment according to FIG. 1.

Figure 7:
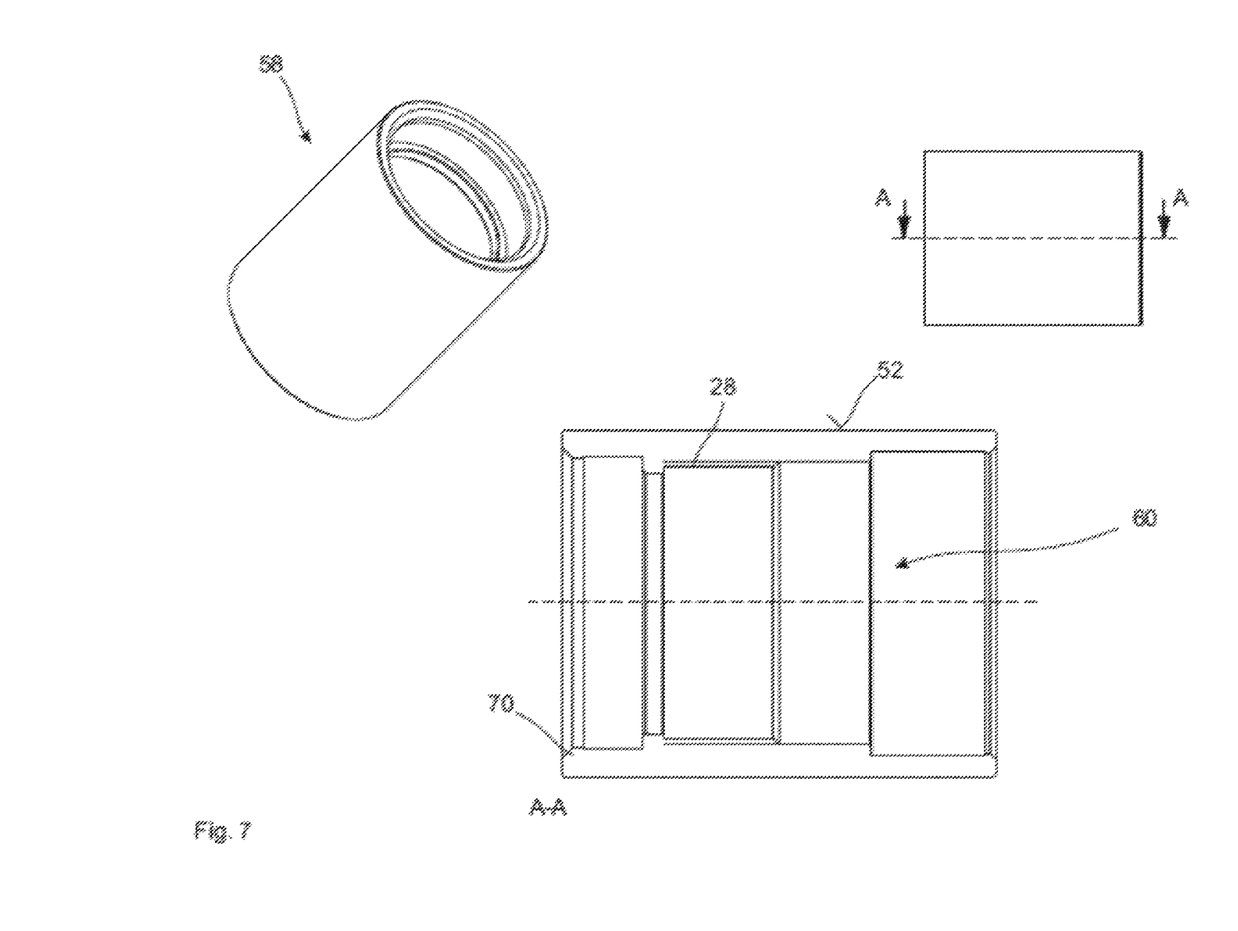
FIG. 7 different representations of a handle piece of the first embodiment.

FIG. 7 shows a handle 58 which comprises the hand guide region 52 of the hand guide element 78. The handle 58 has in turn a fine thread 28 on the inside to receive the receiving element 60 and has corresponding multistage radii to receive the receiving element 60 and for insertion of the actuating element 38. In particular it has a snap ring 70 which serves as a latching hook and limits a travel distance of the actuating element 38 relative to the hand guide element 78.

Figure 8:
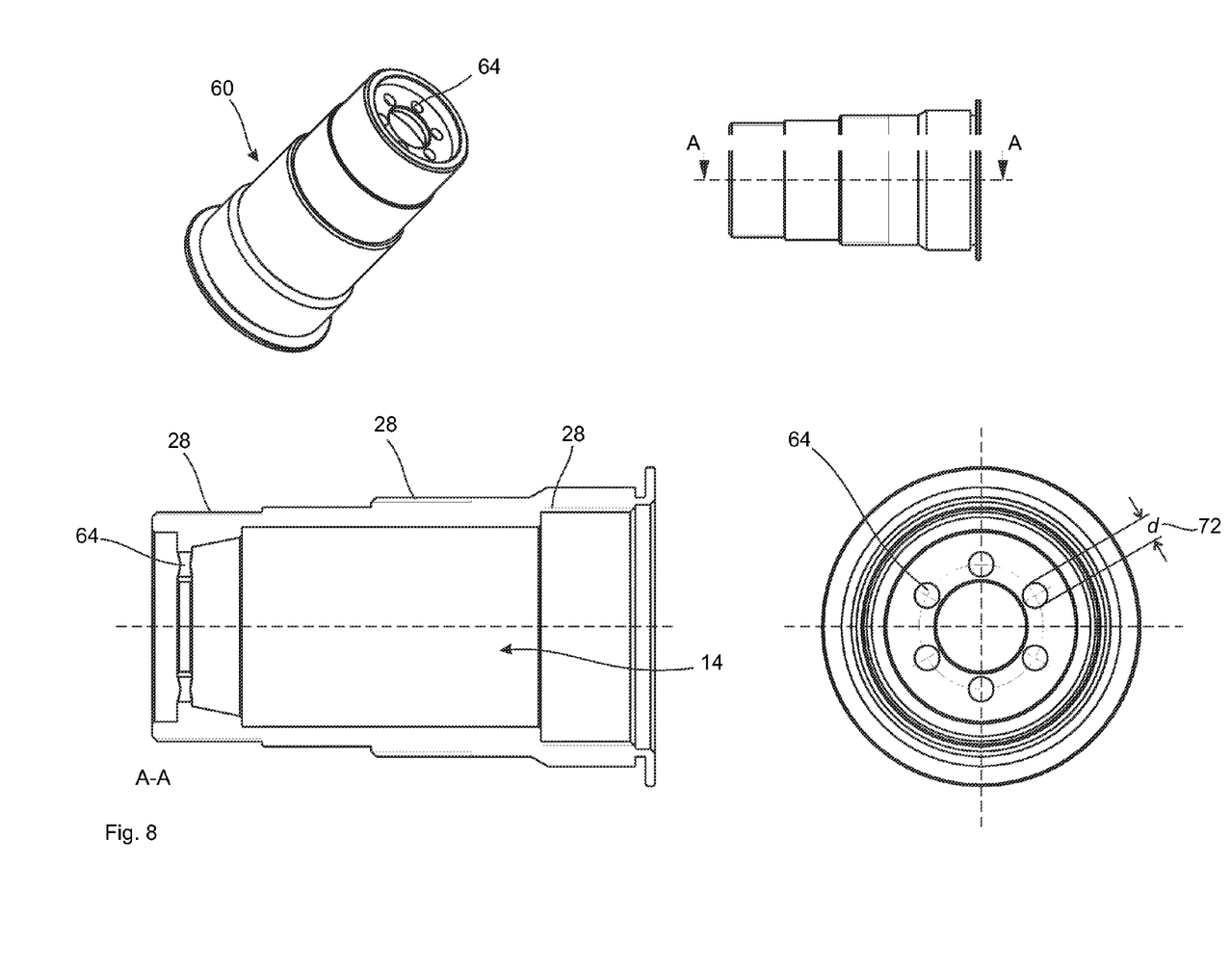
FIG. 8 different representations of a receiving element of the first embodiment.

FIG. 8 shows in perspective in a plan view and a side view and in a sectional view an embodiment of a receiving element 60 of the first embodiment. A receptacle 14 with inserted gas pressure vessel 16 can be screwed into the receiving element 60. For this purpose, the receiving element 60 has an internal thread 28 and two further external threads 28, which serve to screw into the handle 58 and to screwing in the actuating element 38. Furthermore, the receiving element 60 has on its axial upper side a plurality of gas passage apertures 64 having a gas passage aperture diameter d 72. The number and the size of the gas passage apertures 64 essentially determine the outflow rate and outflow time of gas from the inserted gas pressure vessel 16 and hence determine the achievable cooling temperature and cooling duration. For example, a variable adjustability of the aperture diameter d 72 can be varied to adjust the cooling temperature or for repeated use of an inserted gas pressure vessel 16, where a smaller diameter d corresponds to a longer cooling time d at a lower temperature.

Figure 9:
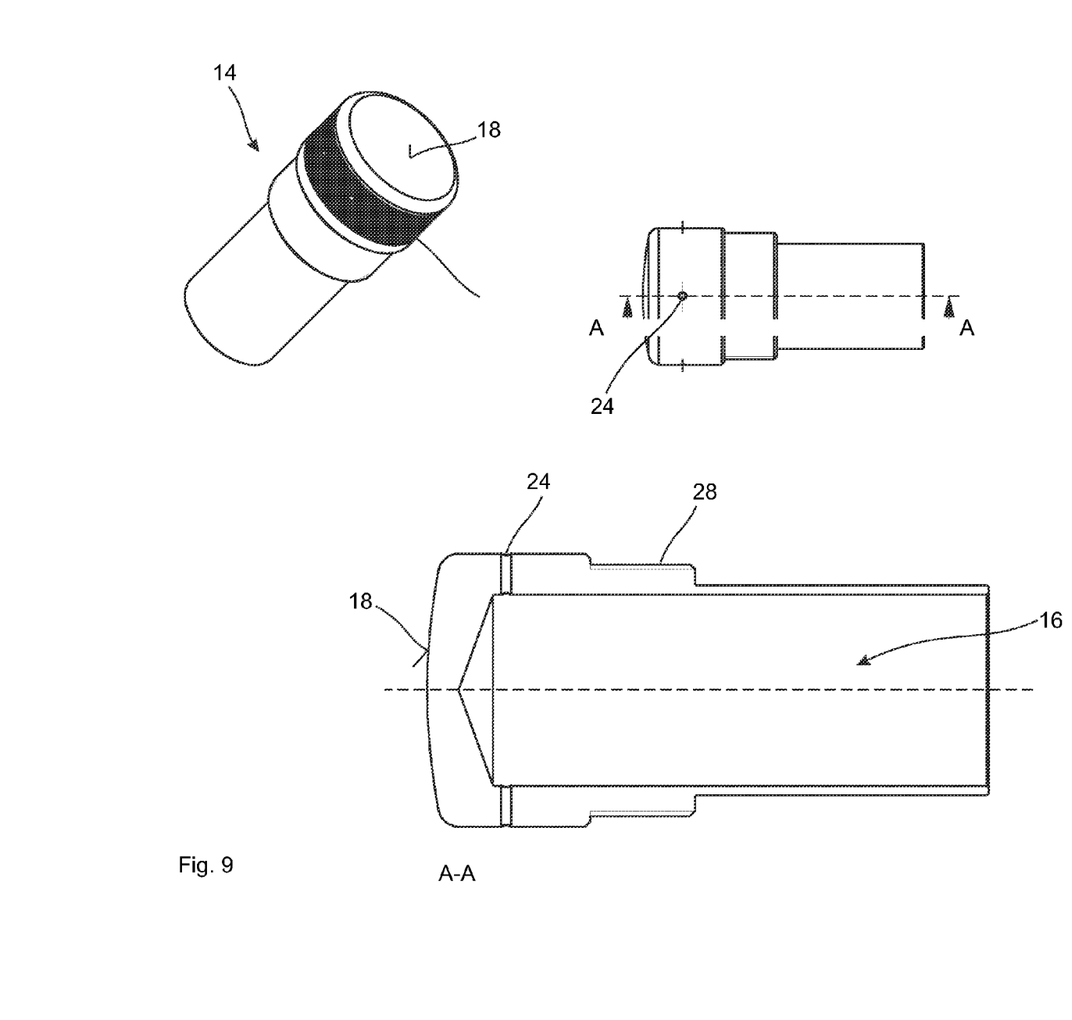
FIG. 9 different designs of a receptacle of the first embodiment.

FIG. 9 shows, both in a perspective view and in a side and sectional view, the embodiment of a receptacle 14 which can be used in the first embodiment of FIG. 1 with gas pressure vessel 16 in place. In contrast to the previously described parts of the cooling device, which are made from materials that are poorly heat-conducting or insulating, the receptacle 14 is constructed of a material that conducts well, in particular a metallic material, where in particular the bottom side with externally arranged cooling surface 18 is of particularly thick material of high thermal conductivity in order to provide a high heat capacity and thermal conductivity. A gas pressure vessel 16 can be received on the bottom side into the interior of the cup-shaped receptacle 14 and screwed into the main body 12 by means of a fine thread on the outer jacket surface 28 of the receptacle 14, in particular into the internal fine thread of the receiving element 60. Upon release of gas from the gas pressure vessel 16, the gas is conducted along a gap between the gas pressure vessel jacket 20 and the internal surface of the receptacle 14 to the gas outlet ducts 24, where it can exit in the vicinity of the cooling surface 18, but does not wet the epidermis to be treated. The cooling surface 18 can be, in particular, slightly curved and convex, but can also be formed flat or concave, depending on the nature of the place to be treated, to exert the highest possible cooling effect or a selective cooling effect. Instead of conducting gas along a gap between the outer jacket surface 20 of the gas pressure vessel 16 and the internal wall of the receptacle 14, additional gas guiding channels can be arranged inside the main body 12 and/or receptacle 14, enabling conduction of the gas and gas release.

Figure 10:
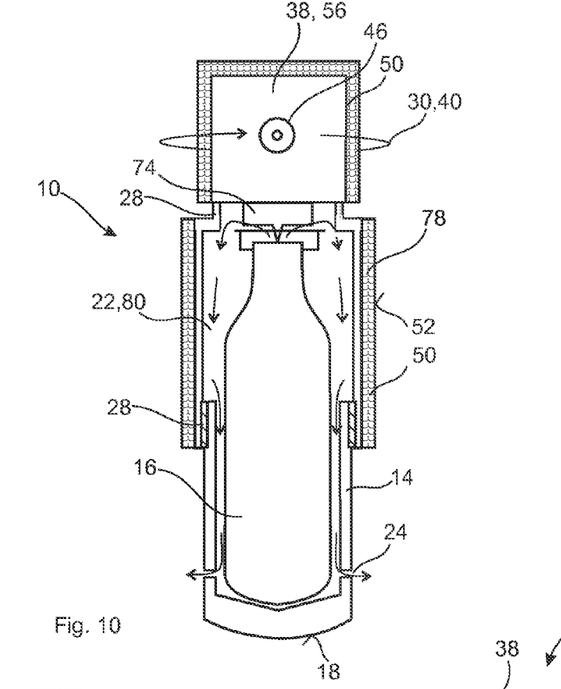
FIG. 10 a schematic section through a second embodiment of a cooling device.

FIG. 10 shows schematically a further embodiment of a hand-operated cooling device 10. Its arrangement corresponds in principle to that shown in FIG. 1 for the first embodiment 10, however, the hand guide region 52 and cap 56 of the actuating element 38 are additionally covered by a heat-insulating material 50 to prevent unintended dissipation of cold from the main body 12. The actuating element 38 is activated by means of a rotary mechanism 30, which pierces a sealing membrane 44 of a gas pressure vessel 16 as a result of a rotational movement by an opening pin 54 of an opening pin element 74, where gas exits, flows along the outer jacket 20 of the gas pressure vessel 16 and emerges at gas outlet ducts 24 at the bottom end of the receptacle 14. Thanks to the heat insulation 50, the entire cold energy dissipated is delivered to an uninsulated region of the cooling surface 18 that conducts heat well and can be used to cool a painful area. To safeguard against an undesired activation of the cooling device 10, a securing element 46, such as a safety pin which has to be pulled out or a safety button which has to be pressed in before a rotational movement 40 of the rotary mechanism 30 can be carried out, is arranged on the actuating element 38.

Figure 11A:
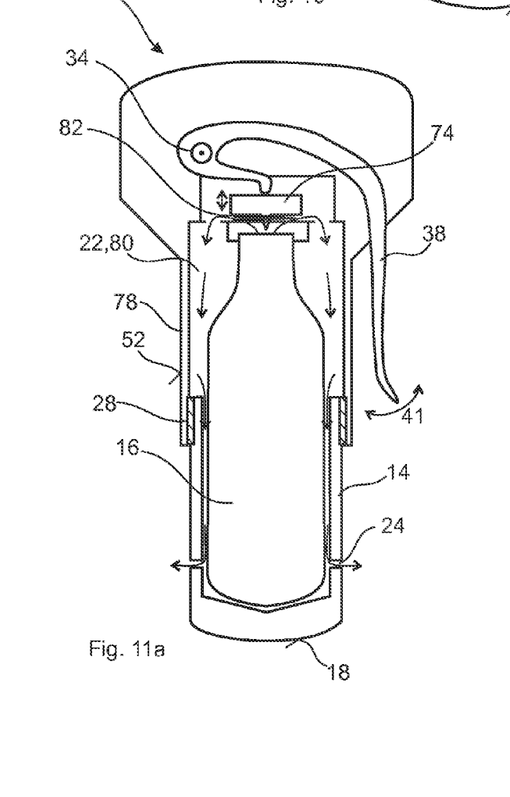
FIG. 11 further schematic representations of embodiments of a hand-operated cooling device.

FIG. 11 shows two further embodiments of a hand-operated cooling device 10, which in their basic design and mode of function correspond to the embodiments shown in FIG. 1/FIG. 10. A description of the same components is therefore omitted. In FIG. 11a a rocker mechanism 34 is provided as actuating element 28, which by means of a rocker pressure movement 41 of a rocker lever causes a penetrative piercing of a sealing membrane 44 of a gas pressure vessel 16 by the opening pin element 74. Upon release of the rocking lever of the actuating element 38, a spring means 82 effects a reset movement, so that was can flow out without hindrance. The outflow of the gas and the structure of the main body 12 and the receptacle 14 correspond here to the versions in the preceding embodiments.

Figure 11B:
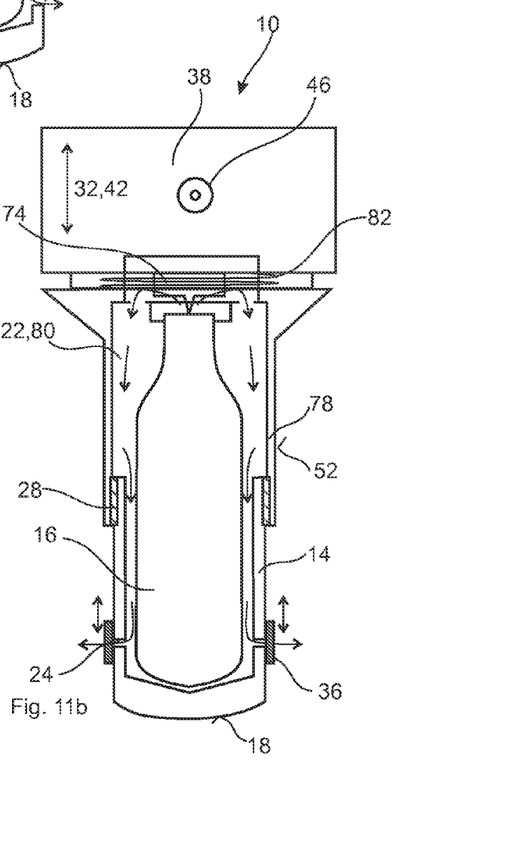

In contrast, FIG. 11b shows a further embodiment in which the actuating element 38 brings about piercing of the sealing membrane 44 of the gas pressure vessel 16 by means of an axial pressure movement 42. In this case too, a spring means 82 ensures a reset movement of the actuating means 38 so that the gas can freely flow out through the pierced sealing membrane. In this case, a shut-off valve 36 is arranged at the gas outlet ducts 24, by the opening or closing of which a gas release can be enabled or prevented. To do so it is necessary for all screw elements or other joining elements of the cooling device 10 to be designed gas-tight, for example by means of seals, so that the pressure prevailing on the inside cannot escape in an unwelcome manner. Opening or closing of the shut-off valve 36 can generate a metered or multiple cooling effect at the cooling surface 18. To prevent an inadvertent activation of the actuating element 38, a securing clement 46 is arranged on the cap 56, where only upon actuation of the securing element 46, for example by pulling out a locking pin or pushing in a locking bolt, a pressure movement can be exerted on the actuating element 38 in order to open the membrane 44 of the gas pressure vessel 16.

The invention proposes a hand-operated cooling device which is portable, which prevents incorrect handling, generates a constant cooling effect, and can be designed to be space-saving and compact for a single usage. Even inexperienced users can produce a therapeutic cooling effect, without inducing cold burns on the areas to be treated. The invention uses a standard gas pressure cartridge, for example, a cream capsule that is available in large quantities and at low cost, where unscrewing the receptacle, inserting the gas cartridge into the receptacle, screwing the receptacle with an inserted cartridge into the main body, rotating the main body using a threaded cap and hence pressing a steel pin into the gas pressure cartridge causes a gas to flow out, where the escaping and expanding gas in the end region of the receptacle creates a cooling effect so that the cooling surface can exert a cooling effect on the area to be treated. The cooling device in accordance with the invention is particularly suitable for carrying around and for the mobile treatment of sports injuries or other comparable cases in which a rapid cooling effect has to be achieved without trained specialist personnel. In particular, the cooling device may be designed so that after opening of the gas pressure vessel a cooling effect can be achieved in about 5 to 10 seconds down to a temperature of approximately 5 to 7° C., where this temperature can be maintained over a period of 3 to 5 minutes. The cooling device is here designed to be very small and hardly larger than the dimensions of the gas pressure vessel itself and prevents an risk of incorrect operation or cold burns. All types of gas pressure vessel containing pressurized air, $N_2O$, $CO_2$ or other gas can be used.

The invention claimed is:

1. Hand-operated cooling device for cryotherapy, comprising a main body and a receptacle that can be at least partially inserted in the main body for the exchangeable receiving and insertion of a gas pressure vessel, where the main body is of a material of low specific thermal conductivity and comprises a gas outlet actuating means which can be actuated manually and bring about outflow of a gas from the gas pressure vessel when the receptacle is in place, wherein the receptacle is of a material of high specific thermal conductivity and comprises a cooling surface that can be cooled by the expansion effect of the outflowing gas inside the cooling device and by the cooling of a gas pressure vessel jacket, where the gas is conducted inside the main body and inside the receptacle by gas conducting means and can exit at the receptacle to the side adjacent to the cooling surface and is conducted away from the cooling surface in such a way that the surface to be cooled is not directly aerated or sprayed with the gas.

2. Cooling device according to claim 1, wherein the receptacle is substantially cup-shaped and is complementary in shape to the bottom region of the gas pressure vessel and is made from a material of high thermal conductivity, where the bottom outer surface of the receptacle forms the cooling surface and the receptacle has at least one gas outlet duct along a circumferential region at the bottom-side end, and the receptacle can accommodate the gas pressure vessel at least in the bottom region substantially in a positive fit to attain heat coupling, where between the inner wall of the receptacle and outer gas pressure vessel jacket outflowing gas can flow from the open end of the receptacle inserted into the main body.

3. Device according to claim 1, wherein the receptacle holding the gas pressure vessel can be inserted into the main body by a screw-fit, snap-fit or a bayonet fit.

4. Device according to claim 1, wherein the gas outlet actuating means comprises a rotating mechanism, a rocker mechanism a press mechanism or a pull mechanism to bring about release of gas from the gas pressure vessel, where after insertion of the gas pressure vessel a rotating, rocker, press or pull movement of an actuating element can actuate the release mechanism of a shut-off valve of the gas pressure vessel or the main body, or can pierce a sealing membrane of the gas pressure vessel.

5. Device according to claim 4, wherein the gas outlet actuating means comprises an opening pin for the penetrative piercing of the sealing membrane of the gas pressure vessel.

6. Device according to claim 3, wherein the main body has at least one gas passage aperture that is designed to reduce the gas exit velocity, where the at least one gas passage aperture has an adjustable aperture diameter d so that the gas outflow velocity and hence the desired cooling temperature can be set in the range 2 to 12° C.

7. Device according to claim 1, wherein a release mechanism comprises a securing element that can prevent inadvertent actuation of the actuating element.

8. Device according to claim 1, wherein the receptacle is suitable for holding a $N_2O$ or $CO_2$ gas pressure vessel with a fill weight of 2 to 350 g which has a length dimension of 4 to 20 cm and a diameter of 1 to 7 cm.

9. Device according to claim 8, wherein the gas pressure vessel is a $CO_2$ 8g cream dispensing cartridge.

10. Device according to claim 1, wherein at least the cooling surface of the receptacle consists of a material of high specific thermal conductivity and the main body and remaining parts consist of a material of low specific thermal conductivity, wherein a hand-guiding region of the main body is additionally heat-insulating by an insulating layer.

11. Device according to claim 4, wherein the gas outlet actuating means comprises an opening pin for the penetrative piercing of the sealing membrane of the gas pressure vessel and wherein the opening pin is enclosed by an opening pin element that consists of steel.

12. Device according to claim 1, wherein the main body is designed in several parts and comprises a cap, a handle, a receiving element, a sealing element, a bell element and an opening pin element, where at least the cap, the sealing element, the bell element and the opening pin element are positively connected to one another to form the gas outlet actuating means and at least the handle and receiving element are positively connected to each other to form a hand guide element that serves to hold the receptacle and for hand guidance of the cooling device by a user, and the gas outlet actuating means is displaceable relative to the hand guide element and is rotatable to perform an actuating movement for a penetrative piercing of a sealing membrane of the received gas pressure vessel.

* * * * *